United States Patent

Matsubara et al.

[11] Patent Number: 5,855,851
[45] Date of Patent: Jan. 5, 1999

[54] APPARATUS FOR TRASFERRING LIQUID HAVING LIQUID LEVEL SENSING FUNCTION

[75] Inventors: Shigeki Matsubara; Kazuhiro Tanaka; Akira Inagaki, all of Hitachinaka, Japan; Bernd Rösicke, Mannheim, Germany

[73] Assignees: Hitachi, Ltd., Tokyo, Japan; Boehringer Mannheim GmbH, Mannheim, Germany

[21] Appl. No.: 892,658

[22] Filed: Jul. 15, 1997

[30] Foreign Application Priority Data

Jul. 19, 1996 [JP] Japan ..................... 8-190551

[51] Int. Cl.[6] .................................................. B01L 3/02
[52] U.S. Cl. .................. 422/100; 73/864.01; 73/864.24; 141/96; 141/130; 436/54
[58] Field of Search .................. 422/100; 73/864.01, 73/864.11, 864.16, 864.21, 864.22, 864.24, 864.25; 436/54, 180; 141/94–96, 130

[56] References Cited

U.S. PATENT DOCUMENTS

| | | |
|---|---|---|
| 3,754,444 | 8/1973 | Ure et al. . |
| 5,045,286 | 9/1991 | Kitajima et al. . |
| 5,212,992 | 5/1993 | Calhoun et al. . |
| 5,304,347 | 4/1994 | Mann et al. . |
| 5,365,783 | 11/1994 | Zweifel . |
| 5,493,922 | 2/1996 | Ramey et al. . |
| 5,550,059 | 8/1996 | Boger et al. . |
| 5,648,727 | 7/1997 | Tyberg et al. . |

FOREIGN PATENT DOCUMENTS

| | | |
|---|---|---|
| 1-178826 | 7/1989 | Japan . |
| 7-43369 | 2/1995 | Japan . |

*Primary Examiner*—Jan Ludlow
*Attorney, Agent, or Firm*—Fay,Sharpe,Beall,Fagan,Minnich & McKee

[57] ABSTRACT

The present invention relates to an apparatus for transferring a liquid capable of accurately performing detection of a liquid level using a pipetting probe even in a case of a high electric conductivity of a in-flow-passage moving fluid which transmits sucking and discharging operation of a syringe (107) to the pipetting probe (100, 400, 500, 600). The probe has a liquid level sensing electrode (103, 401, 501, 601) and an inner tube (102, 402, 502, 602). The liquid level sensing electrode capable of contacting with a liquid to be pipetted is electrically separated from an inner tube filled with the moving fluid, and the both are insulated by an electric insulating member (104B, 403, 503) between them. A container (111) containing the liquid to be pipetted is held by a container holder (112), and a liquid level can be detected by change in an electrostatic capacitance between the container holder and the liquid level sensing electrode of the probe when the probe is moved downward. During sucking the liquid, the inner tube is not brought in contact with the liquid. The inner tube and the container holder are grounded.

9 Claims, 7 Drawing Sheets

APPARATUS FOR TRASFERRING LIQUID HAVING LIQUID LEVEL SENSING FUNCTION

BACKGROUND OF THE INVENTION

The present invention relates to an apparatus for transferring a liquid having a liquid level sensing function, and more particularly relates to an apparatus for transferring a liquid suitable for applying a clinical automatic analyzer for analyzing body fluid samples.

In an automatic analyzer for automatically analyzing biological samples, as a pre-treatment of analysis there is a process in which a sample and a reagent are pipetted and reacted. Further, the reacted reaction solution sometimes needs to be pipetted. It is a necessary condition for accurately performing the measurement of the sample to accurately perform the pipetting work.

In pipetting the sample and the reagent, a pipetting probe is dipped in the sample or the reagent to suck the sample or the reagent into the pipetting probe using a sucking means such as a syringe. Then, the probe having pipetted the sample or the reagent is moved down inside a reaction container to discharge the sample or the reagent in the probe into the reaction container by a discharging operation of the syringe. Pure water is generally used as a medium for transmitting the operation of the syringe to the probe, that is, as an in-flow-passage moving fluid.

The depth of dipping the probe into the sample or the reagent should be minimized. The reason is as follows. Since the sample or the reagent is attached onto the outer surface of the probe when the probe is dipped into the sample or the reagent, the sample or the reagent attached onto the surface must be cleaned. However, if the probe is inserted into the sample or the reagent more deeply than a necessary depth, the outer wall of the probe is not sufficiently cleaned and the remaining fluid attached on the probe may become a source of contamination. Further, a large amount of water cleaning the outer wall of the probe is necessary if the probe is inserted into the sample or the reagent more deeply than a necessary depth, which is not preferable from the viewpoint of economy.

In order to minimize the depth of the probe inserted into the sample or the reagent, it is inevitable to provide a function for detecting that the probe reaches a level of necessary minimum depth in the sample or the reagent, that is, a level detecting function. For this purpose, a liquid level sensor of electrostatic capacitance type disclosed, for example, in Japanese Patent Application Laid-Open No.1-178826 is used. The detection of a liquid surface utilizes the fact that the body fluid sample and the reagent are conductive fluids.

In the liquid level sensor of Japanese Patent Application Laid-Open No.1-178826, the inside of the vertically movable probe is filled with pure water as an in-flow-passage movable fluid, and the sample is sucked into the probe by operation of the syringe. A sample container is placed on a metallic container holder. The probe formed of a single tube is used as a one electrode for detecting a liquid surface, and the container holder is used as the other electrode. The probe serves as the electrode for detecting liquid surface, and the container holder is grounded. An electrostatic capacitance between the electrodes is converted to an electric signal corresponding to the electrostatic capacitance using a converting circuit. Since the electrostatic capacitance between the electrodes changes before the probe is in contact with a liquid surface of the sample and after the probe is in contact with the liquid surface, a detection circuit detects that the probe reaches the liquid surface when the capacitance changes, and the downward movement of the probe is stopped.

A liquid level sensor using a pipetting probe having two tubes is disclosed in Japanese Patent Application Laid-Open No.7-43369. An inner tube is used as an electrode for detecting liquid surface, and an outer tube is used as an electric conductive shield member. The outer tube is grounded. The end of the inner tube is positioned at a level lower than the end of the outer tube so that the inner tube may be brought in contact with a sample to be pipetted. An electric insulator insulates between the inner tube and the outer tube.

In both of the above-mentioned liquid level sensors disclosed in Japanese Patent Application Laid-Open No.1-178826 and in Japanese Patent Application Laid-Open No.7-43369, the inside of the tube used as the electrode for detecting liquid surface is filled with the in-flow-passage movable fluid which is moved by operation of the syringe of pipetting pump. Even if pure water not having electric conductivity is used as the movable fluid, the electric conductivity of the movable fluid is increased due to the breeding of microbes and the whole flow passage becomes electrically conductive when the movable fluid is used for a long period. Thereby, the electrostatic capacitance between the pipetting probe and the container holder becomes large.

Therefore, the electrostatic capacitance between the pipetting probe and the container holder changes as the probe is moved upward or downward. Such change disturbs the measurement of detecting a liquid surface of a liquid to be pipetted.

On the other hand, in a case of analyzing a trace quantity of ingredient in a sample, occurrence of carry-over between samples is a problem. It is known to use disposable nozzle tips in order to avoid this problem. In a case of using disposable nozzle tips made of an electrically conductive plastic, since the electric conductivity is smaller than that in a case where a straight nozzle of non-disposable type made of stainless steel is used as the probe, the liquid level sensing becomes sensitive to the effect of an increase in electric conductivity of the movable fluid.

SUMMARY OF THE INVENTION

An object of the present invention is to provide an apparatus for transferring a liquid in which a liquid having electric conductivity can be used as a movable fluid applied to a pipetting probe.

Another object of the present invention is to provide an apparatus for transferring a liquid in which the change of electric capacitance between a pipetting probe and a container holder is extremely small during a period when the pipetting probe is being moved downward until it comes in contact with a liquid surface.

A further object of the present invention is to provide an apparatus for transferring a liquid having a liquid level sensor in which an electric connection between a movable fluid and a nozzle tip does not occur.

In the present invention, a probe is constructed so that movable fluid moved in the probe by operation of a pipetting pump is not in contact directly with a liquid level sensing electrode of the probe and is also electrically not connected with the liquid level sensing electrode.

That is, the probe in accordance with the present invention has an inner tube and the liquid level sensing electrode, and the liquid level sensing electrode has an outer tube. Just before starting sucking operation of a liquid to be pipetted by the probe, the inside of the inner tube is filled with the moving fluid. The liquid level sensing electrode is into contact with the liquid to be pipetted, but the inner tube does not come in contact with the liquid.

The terminal end of the liquid level sensing electrode is arranged so as to be positioned at a level lower than the level of the terminal end of the inner tube, and the inner tube is arranged so that the liquid taken into the probe does not come into contact to the inner tube. Further, the liquid level sensing electrode and the inner tube are electrically insulated between them.

In a preferred embodiment of the present invention, the inner tube is made of an electrically conductive material, and the inner tube is in the same electric potential with the container holder.

The apparatus for transferring a liquid comprises an electrically conductive container holder for holding a container containing a liquid to be pipetted, a probe for pipetting part of the liquid in the container, a pipetting pump connected to the probe, the pump being capable of sucking the liquid into the probe by moving the movable fluid in the probe, and a device for outputting a signal detecting the liquid surface of the liquid on the container based on a change in electrostatic capacitance between the container holder and the probe.

In a preferred embodiment, the liquid level sensing electrode has an electrically conductive nozzle tip, and the nozzle tip is detachably connected to the outer tube. The liquid level sensing electrode has a hollow compartment for receiving a liquid from a container, and the inner tube is arranged so that the end of the inner tube is exposed in the hollow compartment. The inner tube is made of an electrically conductive material, and the container holder and the inner tube are grounded. Further, there is provided a means for measuring an electric potential between the liquid level sensing electrode and the inner tube in order to check an electric connection between the liquid level sensing electrode and the inner tube.

DETAILED DESCRIPTION OF THE PREFERRED EMBODIMENTS

Figure 1:
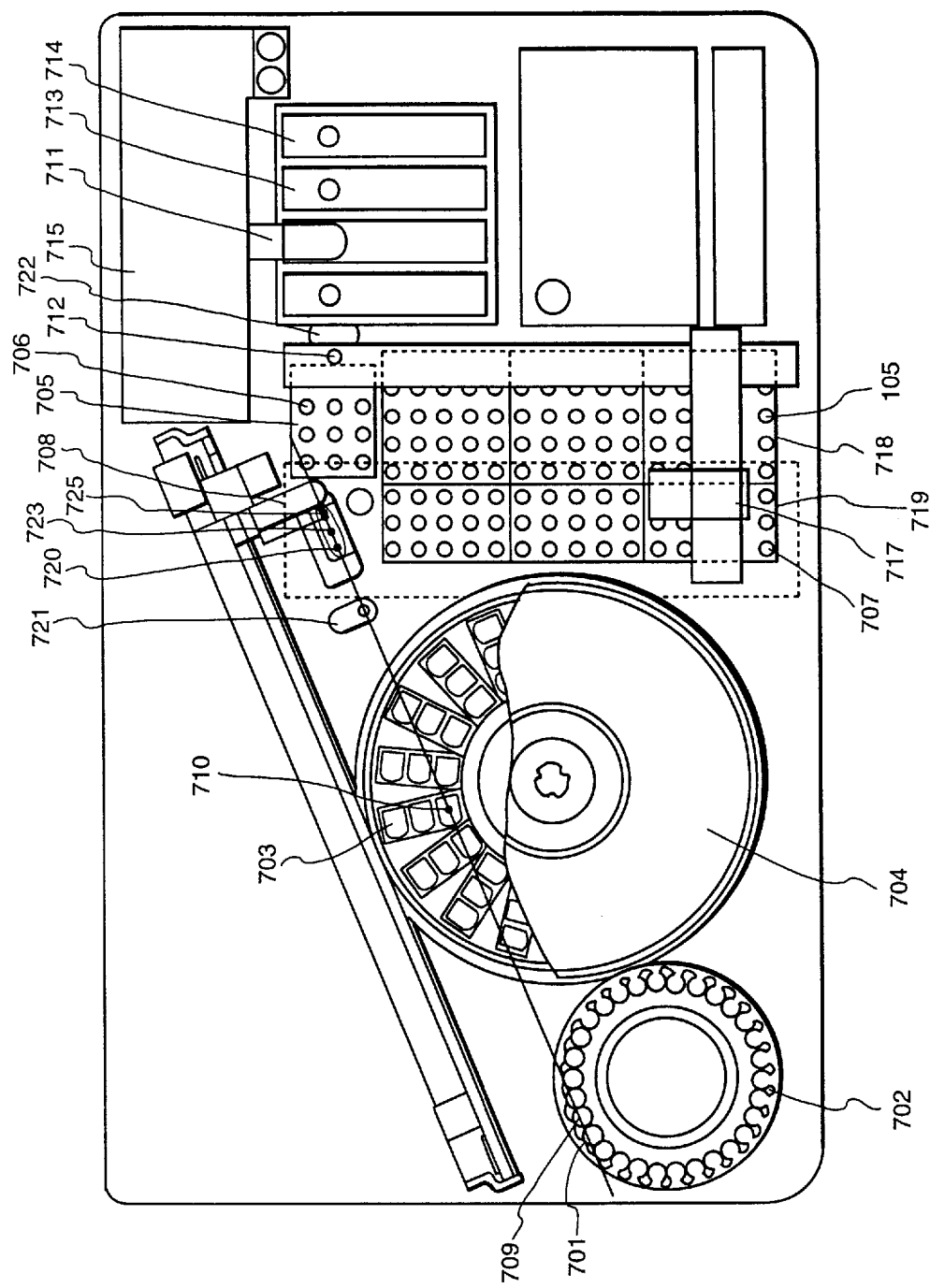
FIG. 1 is a plan view showing an embodiment of an automatic analyzer to which the present invention is applied.

FIG. 1 is a view showing an example of an automatic analyzer to which an apparatus for transferring a liquid in accordance with the present invention is applied. Referring to the figure, a plurality of sample containers 701 are arranged on a sample disk 702 which can be rotated using a motor. These sample containers 701 are detachably mounted onto the sample disk 702 which forms container holders. Similarly, a plurality of reagent bottles 703 are arranged on a reagent disk 704 which can be rotated using a motor. The reagent disk 704 has a plurality of container holders. Reaction containers 707 are stored in a reaction position 706. A pipetter arm 708 having a probe can be moved from an upper portion of a sample sucking position 709 to an upper portion of a reaction container receiving position 723, and from an upper portion of a reagent sucking position 710 to the upper portion of the reaction container receiving position 723 using a motor, and further can be moved vertically at each of the positions. A sipper 711 can be freely moved among an upper portion of a reaction solution sucking position 712, an upper portion of a buffer solution sucking position 713 and an upper portion of an in-flow-cell cleaning liquid sucking position 714 using a motor, and also can be vertically moved at each of the positions. Further, the sipper 711 has a function to transfer a reaction solution to a flow cell in a detecting unit 715 through a tube. A transferring mechanism 717 for tip and reaction container transfers an unused disposable nozzle tip 105 from a tip storing position 718 to a tip connecting position 720, an unused disposable reaction container 707 from a reaction container storing position 719 to a reaction container receiving position 723, the reaction container 707 added with a sample and a reagent from the reaction container receiving position 723 to the reaction position 706 in a constant temperature bath 705, and further the reaction container 707 after incubation from the reaction position 706 to the reaction solution sucking position 712.

Figure 2A:
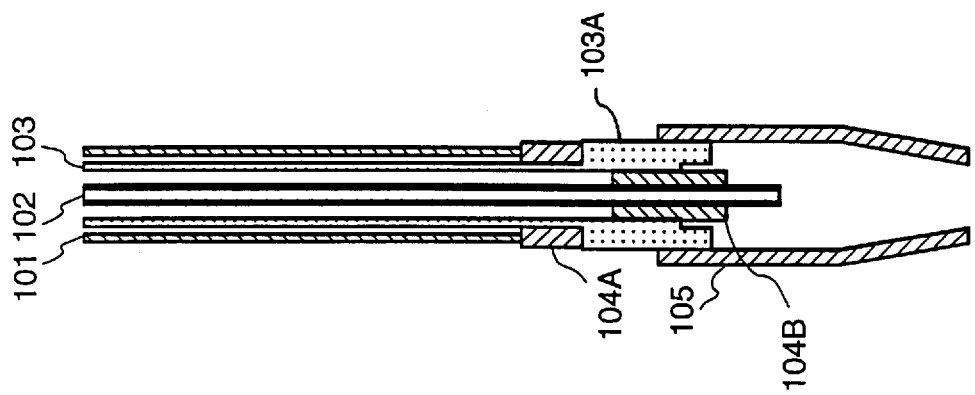
FIG. 2A is a schematic view showing the construction of an apparatus for transferring a liquid used in the analyzer of FIG. 1.
Figure 2B:
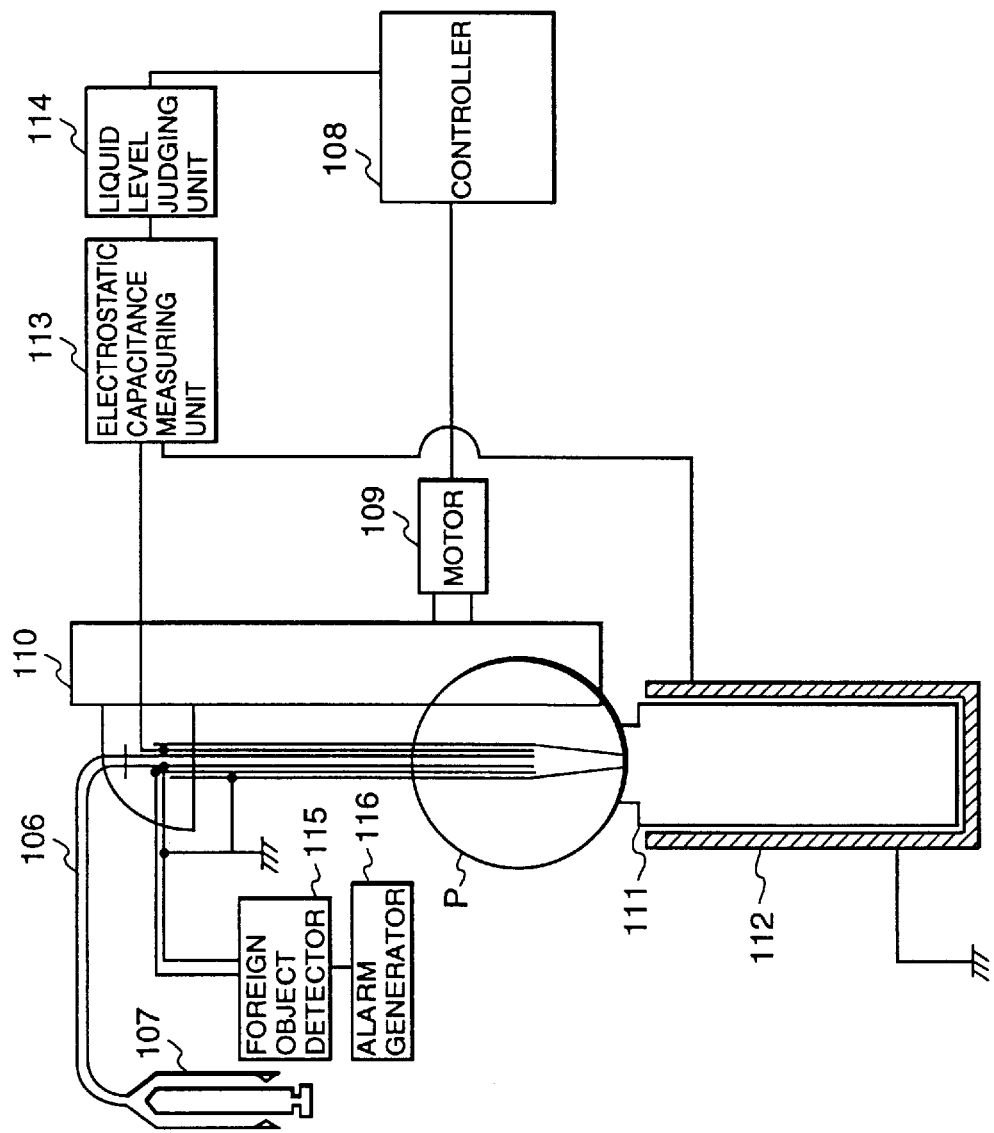
FIG. 2B is an enlarged view of the probe in FIG. 2A.

The analyzer has an apparatus for transferring a liquid as shown in FIG. 2A, and a pipetting probe 100 as shown in FIG. 2B is attached to the pipetter arm 708. The probe 100 has an inner tube 102 containing a moving fluid, a liquid level sensing electrode 103 and an electrostatic capacitance shield member 101. The sample disk 702, the reagent disk 704, the inner tube 102 and the electrostatic capacitance shield member 101 are grounded. By doing so, the container holders in the disks 702 and 704 are grounded. The unused nozzle tip 105 is connected to the outer tube 103A of the probe 100 at the tip connecting position 720 prior to starting sucking operation of a sample and/or a reagent.

The sipper 711 has a liquid level sensor which has a structure different from that of the liquid level sensor in accordance with the present invention. Each of the units is time-controlled to be operated by a controller 108.

Process of the automatic analyzer shown in FIG. 1 will be described below. Initially, the transferring mechanism 717 for tip and reaction container transfers an unused disposable nozzle tip 105 to the tip connecting position 720 and an unused reaction container 707 to the reaction container receiving position 723. The sample disk 702 is rotated so that a sample container 704 containing a sample to be analyzed is positioned at the sample sucking position 709. At the same time, a reagent disk 704 is rotated so that a reagent bottle containing a reagent used for the analysis is positioned at the reagent sucking position 710. At the same time, an unused nozzle tip is connected to the pipetting probe 100 at the upper portion of the tip connecting position 720, and then the pipetter arm 708 is moved to the reagent sucking position. The pipetter arm 708 is moved down at the reagent sucking position 710 and the liquid level sensor is actuated to stop the operation of downward movement when the top end of the disposable nozzle tip 105 reaches the liquid surface of the reagent. At this position, the reagent is sucked in the nozzle tip 105 of the probe 100. Then, the pipetter arm 708 is moved upward and to a probe cleaning position 721. As the probe 100 reaches the probe cleaning position 721, cleaning water comes out from a cleaning unit to clean the nozzle all of the nozzle tip 105. After that, the pipetter arm 708 is moved to the upper portion of the sample sucking position 709 on the sample disk 702. The pipetter arm 708 is moved down at the sample sucking position 709 and the liquid level sensor is actuated to stop the operation of downward movement when the disposable tip 105 reaches the liquid surface of the sample. At this position, the pipetter 708 sucks the sample. Then, the pipetter arm 708 is moved upward and moved to the upper portion of the reaction container receiving position 723. After that, at the reaction container receiving position 723, the pipetter arm 708 is moved downward and stopped at an appropriate level to eject the mixed solution of the sample and the reagent into a reaction container 707. After ejecting the mixed solution, the pipetter arm 708 is moved upward and moved to a tip disposing position 725. At the tip disposing position 725, the nozzle tip 105 detached from the outer tube 103A of the probe 100 is disposed. Then, the transferring mechanism 717 transfers the reaction container 707 containing the mixed solution from the reaction container receiving position 723 to the reaction position 706.

After elapsing an appropriate time for reaction, the sipper 711 is moved to the upper portion of the buffer solution sucking position 713. The sipper 711 is moved downward and the liquid detector is actuated to stop operation of downward movement when the top end of the sipper reaches the liquid surface of the buffer solution. Then, the buffer solution is sucked. After that, the top end portion of the sipper 711 is cleaned at a sipper cleaning position 722.

The transferring mechanism 717 further transfers the reaction container 707 after passing an incubation time from the reaction position 706 to the reaction solution sucking position 712. The sipper 711 sucks the reaction solution at the reaction solution sucking position 712. After sucking the reaction solution, the sipper 711 is moved to the buffer solution sucking position 713 to suck the buffer solution. The buffer solution and the reaction solution are introduced into a flow cell in the detecting unit 715 through a tube to be measured. Then, the sipper 711 sucks a cleaning liquid at the in-flow-cell cleaning liquid sucking position 714 to clean the inside of the flow cell in the detecting unit 715 through the tube.

FIG. 2A shows an embodiment of an apparatus for transferring a liquid to which the present invention is applied, and FIG. 2B is a cross-sectional view of a pipetting probe used in FIG. 2A. The inner tube 102 of the probe 100 is connected to the syringe 107 through a connecting tube 106, and the inside of the inner tube 102 is filled with water supplied from a cleaning water supply tank 121 through a switching valve 120. The water in the inner tube 102 of the pipetting probe 100 and the connecting tube 106 is moved inside the flow passage by operation of the syringe 107 serving as a pipetting pump, and functions as a movable fluid necessary for the pipetting operation.

The pipetting probe 100 has the inner tube 102, the liquid level sensing electrode and the electric conductive shield member 101. The probe 100 is fixed to the pipetter arm 708. The liquid level sensing electrode 103 has the outer tube 103A coaxial to the inner tube 102 and the disposable nozzle tip 105. The outer diameter of the lower end portion of the outer tube 103A is determined so as to be closely engaged with the top portion of the nozzle tip 105. The outer tube 103A is electrically connected to one of the input terminals of a measuring unit 113 through a lead wire. The electrically conductive shield member 101 in the probe 100 is also cylindrical, and therefore the probe has a coaxial triple-tube structure.

A container 111 such as the sample container 701 or the reagent container 703 is contained in the container holder 112 made of a metal of electrically conductive material. When the container 111 is set in the sample disk 702 or the reagent disk 704, the outside of the container 111 is partially covered by the container holder 112. The container holder is grounded and connected to the other of the input terminals of the measuring unit 113 through a lead wire.

The electrically conductive shield member 101, the inner tube 102 and the liquid level sensing electrode 103 are made of a metallic conductive material such as stainless steel, and electric insulating members 104A and 104B made of polybuthylene-terephtharate (PBT) or the like electrically insulate between the shield member 101 and the sensing electrode 103 and between the inner tube 102 and the sensing electrode 103, respectively. Further, the shield member 101 and the inner tube 102 are grounded.

A liquid to be pipetted such as a sample, a reagent or a reaction solution of a sample and a reagent is sucked in the nozzle tip 105 forming the sensing electrode 103. The nozzle tip 105 is detachable to the outer tube 103A and disposable. The nozzle tip 105 is made of an electrically conductive material such as an electrically conductive plastic. By using the disposable tip 105, it is possible to prevent mutual mixing between samples, between reagents and between a sample and a reagent, and accordingly it is possible to analyze more accurately. Further, since most part of the outer tube 103A except for the top end portion is covered with the electric conductive shield member 101, exposed area of the sensing electrode 103 is minimized. Thereby, the electrostatic capacitance between the container holder 112 of the other electrode for detecting liquid surface and the sensing electrode 103 is less affected by an electrostatic capacitance change in the other portions. Furthermore, since the electric conductive shield member 101 exists, it is possible to prevent erroneous operation of the liquid level sensing due to noise from outside caused by a motor 109 and so on.

There are sometimes formed bubbles in the flow passage of the inner tube 102 or the connecting tube 106 during repeating sucking operation many times. When the bubbles are formed, operation of a syringe 107 cannot be correctly transmitted to the end of the probe due to cushion effect of the bubbles. It is necessary to allow water to flow through in the flow passage periodically in order to remove the bubbles to maintain accuracy of sucking amount and ejecting amount. However, in a case of a common probe not applying the present invention, when water is ejected through the end of the probe, water droplets attach to the end of the probe and the sample or the reagent is diluted by the falling of the water droplets into the container during a sucking operation, which causes a problem of accurate analysis. Further, even in a case of a multi-tube structure, when the moving fluid has a high electric conductivity, the outer tube 103A and the inner tube 102 may be brought into conduction by the droplets attached to the end of the probe.

In the pipetting probe 100 of FIG. 2B, the end of the inner tube 102 is projecting to the end of the outer tube 103A. That is, the end of the inner tube 102 is placed at a level lower than the end of the outer tube 103A. The projecting portion of the inner tube 102 is exposed inside the hollow compartment formed by the nozzle tip 105. Thereby, since the surface area of the end of the tube containing the moving fluid is made small, water droplets are hardly attached there. Furthermore, the lower end of an electric insulator member 104B is projected from the outer tube 103A and exposed to the hollow compartment inside the nozzle tip 105. Since the end of the inner tube 102 is kept a distance from the outer tube 103A by such a construction, electric continuity between the inner tube 102 and the outer tube 103A can be prevented even if water droplets attach to the top end of the inner tube.

The probe 100 can be vertically moved by a probe vertical moving mechanism 110. A container 111 containing a liquid to be pipetted is stored in the container holder 112. The container holder 112 is made of a conductive material such as aluminum and grounded. The sensing electrode 103 and the container holder 112 are connected to an electrostatic capacitance measuring unit 113 as two electrodes for an electrostatic capacitance type liquid level sensor. Further, a liquid surface judging unit 114 is connected between the electrostatic capacitance measuring unit 113 and a control unit 108.

Operation will be described below. The probe 100 connected the nozzle tip 105 is moved downward by the vertical moving mechanism 110 to suck the liquid contained in the container 111. The electrostatic capacitance measuring unit 113 measures an electrostatic capacitance between the sensing electrode 103 and the container holder 112 and the corresponding output signal is transferred to the liquid surface judging unit 114. When the top end of the nozzle tip 105 contacts to the liquid surface, the liquid surface judging unit 114 transmits a liquid surface detecting signal to the controller 108. As the controller 108 receives the liquid surface detecting signal, the controller 108 stops rotation of the motor 109 to stop downward movement of the probe 100. In this state, a predetermined amount of the liquid in the container 111 is sucked into the hollow portion of the nozzle tip 105 by sucking operation of the syringe 107. The liquid is not in contact with the inner tube 102. After that, the probe 100 is moved upward and transferred to the reaction container receiving position 723 of FIG. 1, and again moved downward, and then the liquid contained in the nozzle tip 105 is discharged in a reaction container 707. The connecting tube 106 and the inner tube 102 are filled with a movable medium (liquid) such as water or the like, and accordingly sucking of the liquid into the nozzle tip and discharging of the sucked liquid from the nozzle tip 105 are performed by the movable fluid serving as the sucking and discharging medium moving in the flow passage corresponding to operation of the syringe 107. In a case of sucking a liquid to be pipetted into the nozzle tip 105, the control unit 108 controls vertical movement of the probe 100 and operation of the syringe 107 so that the liquid surface of the liquid sucked in the nozzle tip does not contact to the inner tube 102 and the moving medium inside the inner tube.

On the other hand, when the nozzle tip 105 is disposed after discharging the sucked liquid, there are some cases in that a small amount of liquid remaining at the end portion of the nozzle tip due to depressurization inside the nozzle tip is fly off and the flown-off liquid brings the sensing electrode 103 and the inner tube 102 in an electric connection to be unable to detect a liquid surface. A foreign object detector 115 measures an electric potential between the sensing electrode 103 and the inner tube 102 and recognizes from change in the electric potential that an object (liquid) is attached to the top end of the nozzle tip. By using the foreign object detector 115, it is possible to detect in real time by detecting the change in the electric potential that the outer tube 103A and the inner tube 102 are brought in conduction. Further, in this case, a signal is transmitted from the foreign object detector 115 to an alarm generator 116 to generate an alarm. Corresponding to the alarm, the control unit 108 controls operation of the syringe 107 so as to perform cleaning operation.

Figure 3A:
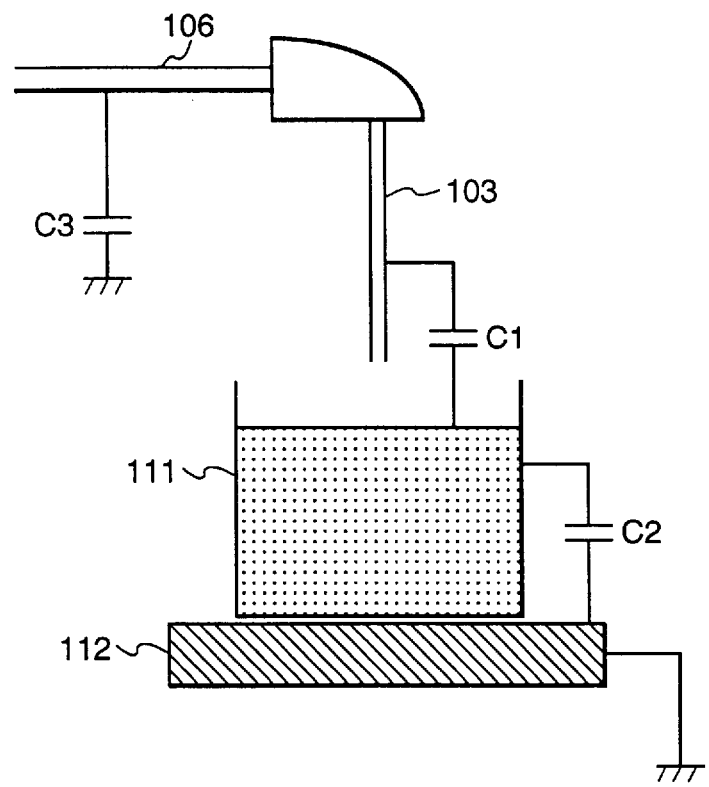
FIG. 3A is a schematic diagram explaining the distribution of electrostatic capacitance in a conventional liquid surface detecting sensor.
Figure 3B:
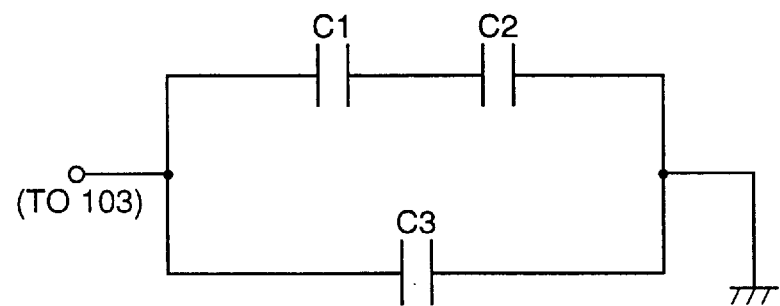
FIG. 3B is a diagram showing the equivalent circuit for the construction of FIG. 3A.

FIG. 3A shows distribution of electrostatic capacitance in the portion of a liquid level sensor employed in a conventional apparatus for transferring a liquid, and FIG. 3B shows the equivalent circuit. In FIG. 3A and FIG. 3B, the reference character C1 indicates an electrostatic capacitance between the sensing electrode 103 and the liquid surface in the container 111, the reference character C2 indicates an electrostatic capacitance between the container holder 112 (grounded) and the liquid in the container 111, and the reference character C3 indicates an electrostatic capacitance between the movable medium filling the connecting tube 106 and the other grounded positions of the apparatus. In a case where the movable fluid is pure water, assuming that the electric conductivity of pure water is 0, $C3=0$. When the pipetting probe is not in contact with the liquid surface, the electrostatic capacitance Ca between the sensing electrode 103 composed of the whole probe and the ground becomes a composite capacitance Ca of C1 and C2, that is, $Ca=C1C2/(C1+C2)$. When the probe is brought in contacts with the liquid surface, the electrostatic capacitance Ca between the sensing electrode 103 and the container holder 112 is given by $Ca=C2$. Therefore, change $\Delta Ca$ in the electrostatic capacitance when the probe contacts to the liquid surface is given by $\Delta Ca=(C2)^2/(C1+C2)$. On the other hand, when the electric conductivity of the movable fluid of water in the connecting tube 106 is increased, the electrostatic capacitance C3 between the water in the connecting tube 106 and the ground cannot be neglected since the sensing electrode 103 are in contact with the water in the connecting tube 106. The electrostatic capacitance Cb between the sensing electrode 103 and the container holder 112 is given by $Cb=C1C2/(C1+C2)+C3$. Further, since the C3 is varied by operation of the connecting tube 106, it is difficult to accurately measure the change in the electrostatic capacitance at contacting of the probe to the liquid surface.

Figure 4A:
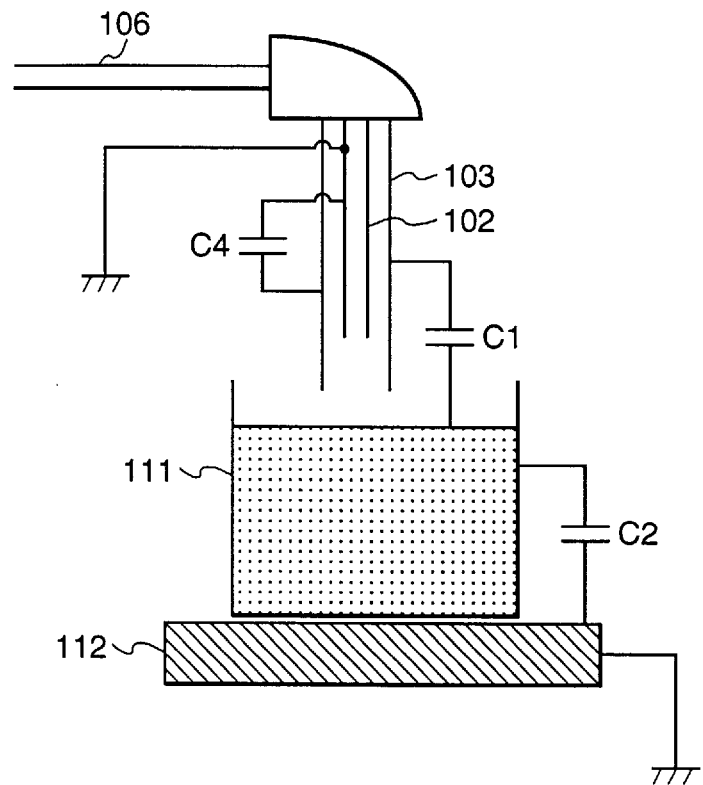
FIG. 4A is a schematic diagram explaining the distribution of electrostatic capacitance in a liquid surface detecting sensor to which the present invention is applied.
Figure 4B:
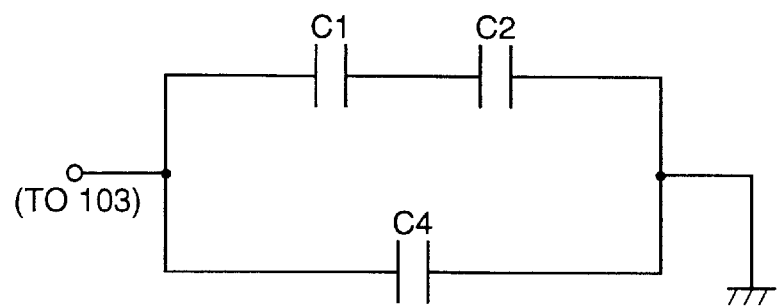
FIG. 4B is a diagram showing the equivalent circuit for the construction of FIG. 4A.

On the other hand, FIG. 4A shows the distribution of electrostatic capacitance of a liquid level sensor in an apparatus for transferring a liquid to which the present invention is applied, and FIG. 4B shows the equivalent circuit. In FIG. 4A and FIG. 4B, the reference character C1 indicates an electrostatic capacitance between the sensing electrode 103 and the liquid surface in the container 111, the reference character C2 indicates an electrostatic capacitance between the container holder 112 (grounded) and the liquid in the container 111, and the reference character C4 indicates an electrostatic capacitance between the sensing electrode 103 and the inner tube 102 (grounded). In this case, the measured electrostatic capacitance is irrespective of the electric conductance of the water in the connecting tube 106 including the flow passage. The electrostatic capacitance Cx between the probe and the ground is given by Cx=C1C2/(C1+C2)+C4, and C4 is constant. Therefore, it is always possible to accurately measure the change in the electrostatic capacitance $\Delta Cx=(C2)^2/(C1+C2)$ at a time when the sensing electrode 103 comes in contact with a liquid surface. In a case of using the disposable nozzle tip 105, in an example of a liquid level sensor according to the conventional technology, liquid surface can be detected only when the electric conductivity of the moving fluid of water in the connecting tube 106 is lower than 1 $\mu$S/cm. However, in the embodiment of the liquid level sensor in accordance with the present invention, it is possible to detect liquid surface regardless of the electric conductivity of the moving liquid of water in the connecting tube 106.

Figure 5:
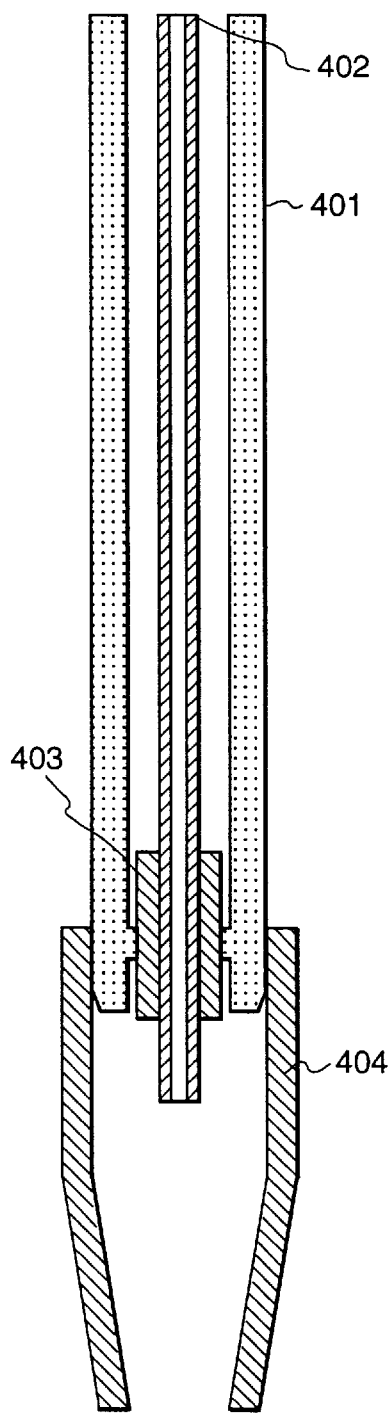
FIG. 5 is a cross-sectional view showing a modified embodiment of a probe.

FIG. 5 shows a modified embodiment of a pipetting probe used in an apparatus for transferring a liquid in accordance with the present invention. This probe 400 is of a coaxial double tube construction of an outer tube 401 and an inner tube 402. Each of the outer tube 401 and the inner tube 402 is made of an electrically conductive material, and are electrically insulated by an electric insulator material 403 between them. The inner tube 402 is grounded. A detachable disposable nozzle tip 404 is connected to near the top end of the probe 400, and liquid is sucked in the inside space portion of the nozzle tip 404. The other parts except for the probe 400 and the operation are the same as those in the apparatus of FIG. 2A. The construction of the probe of FIG. 5 is simple in a point that the probe does not have the electrically conductive shield member 101 shown in FIG. 2B.

Figure 6:
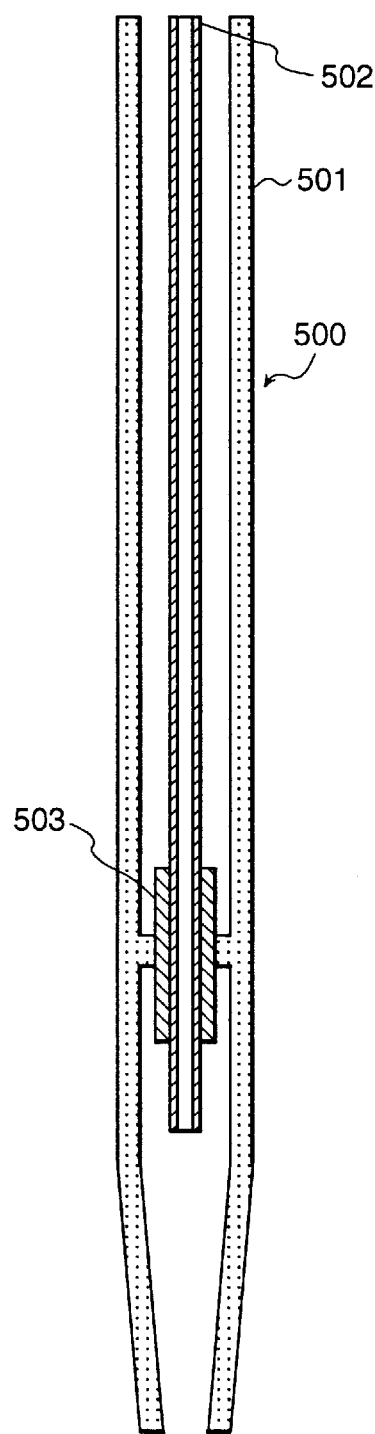
FIG. 6 is a cross-sectional view showing another modified embodiment of a probe.

FIG. 6 shows another modified embodiment of a probe used in an apparatus for transferring a liquid in accordance with the present invention. This probe 500 is of a coaxial double tube construction of an outer tube 501 serving as a sensing electrode and an inner tube 502 serving as a movable fluid tube. Each of the outer tube 501 and the inner tube 502 is made of an electrically conductive material, and the outer tube 501 and the inner tube 502 are electrically insulated by an electric insulator material 503 between them. The inner tube 502 is grounded. FIG. 6 shows an example of a probe without using disposable nozzle tip, and the liquid to be pipetted is sucked in the inside space portion formed by the outer tube near the top end portion of the outer tube. In this case, the sucked liquid is not in contact with the inner tube 502. The other parts except for the probe 500 and the operation are the same as those in the apparatus of FIG. 2A.

Figure 7:
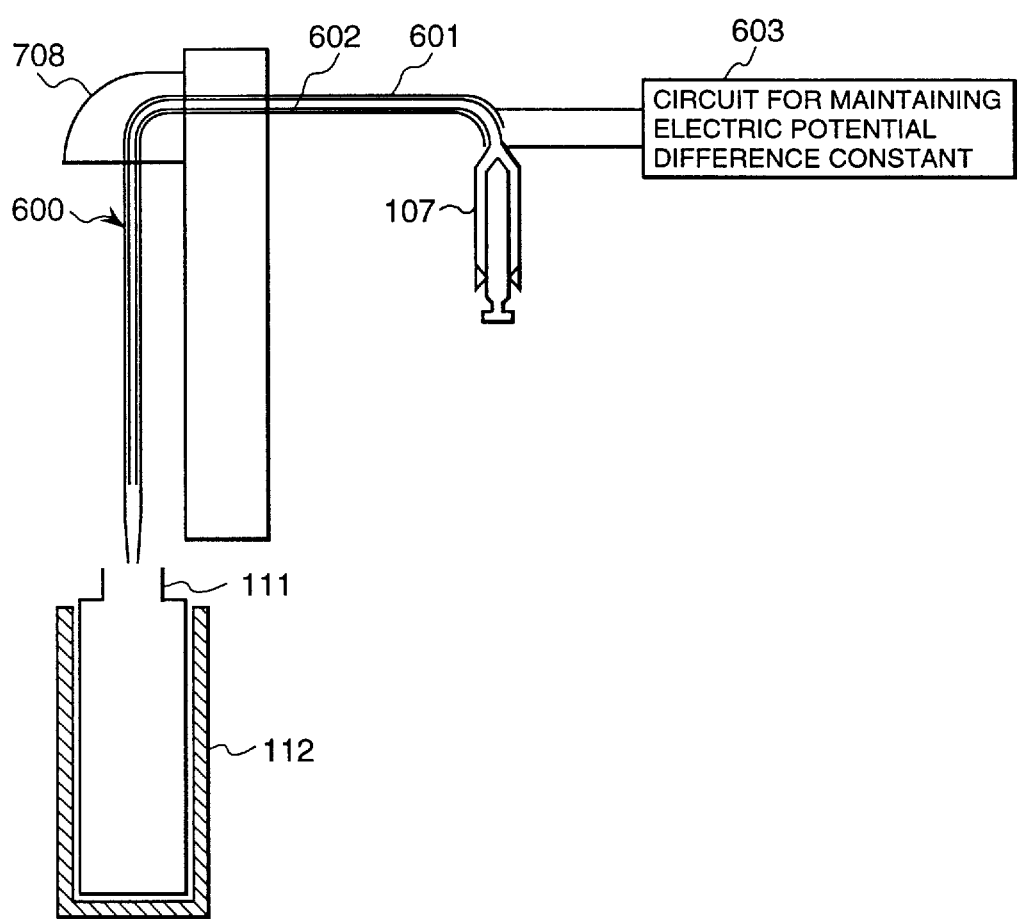
FIG. 7 is a view showing the construction of the main portion of another embodiment of an apparatus for transferring a liquid of which construction of flow passage of moving fluid is modified.

FIG. 7 shows the main portion of another embodiment of an apparatus for transferring a liquid in accordance with the present invention. In this embodiment, an outer tube 601 serving as a sensing electrode and an inner tube 602 serving as a moving fluid tube are formed a coaxial state, extended up to near the syringe 107 so as to include a probe 600 and a connecting tube, and a circuit 603 for maintaining an electric potential between the outer tube and the inner tube at a constant is connected between them. According to this construction, the electrostatic capacitance between the outer tube 601 and the inner tube 602 can be maintained at a constant, and consequently it is possible to prevent the effect of a change in the electrostatic capacitance on the liquid level sensing. In this case, for example, a circuit for maintaining electric potential between coaxial tubes constant disclosed in U.S. Pat. No. 5,304,347 may be employ as the circuit 603 for maintaining electric potential constant.

What is claimed is:
1. An apparatus for transferring a liquid comprising an electrically conductive container holder for holding a container containing a liquid to be pipetted; a probe for pipetting part of the liquid in the container; a pipetting pump connected to the probe, the pump allowing the liquid to be sucked into the probe by moving a movable fluid in the probe; and a device for outputting a signal of detecting a liquid surface of the liquid in the container based on a change in an electrostatic capacitance between the container holder and the probe; wherein said probe comprises an inner tube filled with the movable fluid therein; and a liquid level sensing electrode having an outer tube and being capable of contacting with the liquid to be pipetted;

a terminal end of said liquid level sensing electrode being arranged so as to be positioned at a level lower than a terminal end of the inner tube, the inner tube being arranged so that the liquid taken into the probe is prevented from coming into contact with the inner tube, said liquid level sensing electrode and the inner tube being electrically insulated therebetween.

2. An apparatus for transferring a liquid according to claim 1, wherein said liquid level sensing electrode comprises an electrically conductive nozzle tip, and said nozzle tip is detachably connected to the outer tube.

3. An apparatus for transferring a liquid according to claim 2, wherein the nozzle tip forms a hollow compartment for receiving the liquid in the nozzle tip when the nozzle tip is connected to the outer tube, and the terminal end of the inner tube is projected in said hollow compartment.

4. An apparatus for transferring a liquid according to claim 2, wherein said inner tube is made of an electrically conductive material, and said container holder and said inner tube are the same in electric potential with each other.

5. An apparatus for transferring a liquid according to claim 1, wherein said probe has an electrically conductive shield member for covering said outer tube.

6. An apparatus for transferring a liquid comprising an electrically conductive container holder for holding a container containing a liquid to be pipetted; a probe for pipetting part of the liquid in the container; a pipetting pump connected to the probe, the pump allowing the liquid to be sucked into the probe by moving a movable fluid in the probe; and a device for outputting a signal of detecting a liquid surface of the liquid in the container based on a change in an electrostatic capacitance between the container holder and the probe; wherein said probe comprises an inner tube filled with the movable fluid therein; a liquid level sensing electrode having an outer tube and being capable of coming into contact with the liquid to be pipetted; and an electric insulator member placed between the inner tube and the outer tube;

the inner tube being made of an electric conductive material, the inner tube and the container holder being the same in electric potential with each other.

7. An apparatus for transferring a liquid according to claim 6, which comprises a means for measuring an electric potential difference between said liquid level sensing electrode and said inner tube in order to check an electric conduction state between said liquid level sensing electrode and said inner tube.

8. An apparatus for transferring a liquid according to claim 6, wherein said inner tube and said container holder are grounded.

9. An apparatus for transferring a liquid according to claim 6, wherein said liquid level sensing electrode comprises a hollow compartment for receiving the liquid from said container, and said inner tube is arranged so that a terminal end of the inner tube is exposed in said hollow compartment.

\* \* \* \* \*

UNITED STATES PATENT AND TRADEMARK OFFICE
CERTIFICATE OF CORRRECTION

PATENT NO. : 5,855,851
DATED : January 5, 1999
INVENTOR(S) : Matsubara et al.

It is certified that error appears in the above-identified patent and that said Letters Patent is hereby corrected as shown below:

On the title page insert item [56]

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 0 | 6 | 7 | 0 | 4 | 9 | 7 | 09/06/95 | EPO | | | | |
| | | 0 | 0 | 7 | 2 | 5 | 5 | 8 | 02/23/83 | EPO | | | | |
| | | 0 | 5 | 5 | 5 | 7 | 1 | 0 | 08/18/93 | EPO | | | | |
| | | | | | | | | | | | | | | |

Signed and Sealed this

Sixth Day of April, 1999

Q. TODD DICKINSON

*Attest:*

*Attesting Officer*         *Acting Commissioner of Patents and Trademarks*